(12) United States Patent
Kang

(10) Patent No.: US 9,081,187 B2
(45) Date of Patent: Jul. 14, 2015

(54) MULTIPLE PARALLEL CONFOCAL SYSTEM AND SURFACE MEASUREMENT METHOD USING THE SAME

(71) Applicant: INDUSTRY-ACADEMIC COOPERATION FOUNDATION YONSEI UNIVERSITY, Seoul (KR)

(72) Inventor: Shinill Kang, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/350,578

(22) PCT Filed: Jan. 11, 2013

(86) PCT No.: PCT/KR2013/000256
§ 371 (c)(1),
(2) Date: Apr. 9, 2014

(87) PCT Pub. No.: WO2013/105822
PCT Pub. Date: Jul. 18, 2013

(65) Prior Publication Data
US 2015/0085289 A1    Mar. 26, 2015

(30) Foreign Application Priority Data

Jan. 12, 2012 (KR) .................. 10-2012-0004073

(51) Int. Cl.
*G01N 21/55* (2014.01)
*G02B 21/06* (2006.01)
*G02B 21/00* (2006.01)
(Continued)

(52) U.S. Cl.
CPC ............... *G02B 21/06* (2013.01); *G01B 11/24* (2013.01); *G01N 21/55* (2013.01); *G02B 3/0006* (2013.01); *G02B 21/004* (2013.01); *G01N 2201/06113* (2013.01); *G02B 3/0056* (2013.01)

(58) Field of Classification Search
CPC .... G02B 21/06; G02B 3/0006; G02B 21/004; G02B 3/0056; G01N 21/55; G01N 2201/06113; G01B 11/24
See application file for complete search history.

(56) References Cited

U.S. PATENT DOCUMENTS

| | | | | |
|---|---|---|---|---|
| 5,650,876 | A * | 7/1997 | Davies et al. ................. | 359/622 |
| 5,963,667 | A * | 10/1999 | Hashimoto et al. ........... | 382/190 |
| 6,392,752 | B1 * | 5/2002 | Johnson ........................ | 356/511 |

(Continued)

OTHER PUBLICATIONS

International Search Report for International Application No. PCT/KR2013/000256.

(Continued)

*Primary Examiner* — Kara E Geisel
*Assistant Examiner* — Dominic J Bologna
(74) *Attorney, Agent, or Firm* — LRK Patent Law Firm

(57) ABSTRACT

The present invention relates to a multiple parallel confocal system including: a light source for irradiating light; a relay lens unit through which the light traveling toward a measuring object or the light reflected from the measuring object is passed, the relay lens unit having one or more lens for focusing the light irradiated from the light source; a multiple optical probe having a microlens array on which a plurality of microlenses is arranged, the microlenses into which the focused light through the relay lens unit is incident; and a photo detector for detecting the incident light reflected from the measuring object and passed through the microlenses and the relay lens unit.

12 Claims, 20 Drawing Sheets

(51) Int. Cl.
*G01B 11/24* (2006.01)
*G02B 3/00* (2006.01)

(56) References Cited

U.S. PATENT DOCUMENTS

| | | | | |
|---|---|---|---|---|
| 6,628,390 | B1* | 9/2003 | Johnson | 356/400 |
| 2005/0099670 | A1* | 5/2005 | Kimura et al. | 359/291 |
| 2005/0231702 | A1* | 10/2005 | Shinoda | 355/67 |
| 2007/0146869 | A1* | 6/2007 | Lauer | 359/368 |

OTHER PUBLICATIONS

Ji Seok Lim et al., "Development of Multi-optical Probe Confocal Microscope for Large Areal Measurement", 2011 The Korean Society of Manufacturing Technology Engineers, Journal of Fall Conference, 2011, p. 33.

Min Young Kim et al., "Array Lens and Pinhole-based Multi-Confocal Robot Vision System : Micro Bump Inspections in Wafer Level Packaging", Journal of the Korean Welding and Joining Society, vol. 29, No. 1, pp. 29-32, Feb. 2011.

* cited by examiner

MULTIPLE PARALLEL CONFOCAL SYSTEM AND SURFACE MEASUREMENT METHOD USING THE SAME

TECHNICAL FIELD

The present invention relates to a multiple parallel confocal system and a surface measurement method using the same.

BACKGROUND ART

Recently, a confocal microscope is a device used to irradiate given wavelength of light to a sample, to pass the reflected light to a confocal aperture like a pinhole, and to detect only the light emitted from the focus of an objective lens through a photo detector.

FIG. 1 is a concept view showing a confocal optical system to which the principle of a general confocal microscope is applied.

Referring to FIG. 1, the confocal microscope includes: a light source 11 for irradiating laser light; a beam splitter 13 for converting the advancing path of the incident light thereinto; an objective lens 15 for focusing the light irradiated from the light source 11 thereto; and a photo detector 19. Further, the confocal microscope includes an aperture 17 disposed between the beam splitter 13 and the photo detector 19 so as to allow only image being in focus to be sent toward the photo detector 19.

The light source 11 irradiates the laser light having the wavelength band adequate to a fluorescent material labeled on the sample so as to induce the emission of the fluorescent material, and the emitted fluorescent signals are focused by the objective lens 15. Next, the focused fluorescent signals are focused to the photo detector 19 via the beam splitter 13. At this time, the image being not in focus is blocked by the aperture 17, and therefore, the fluorescent signal image being in focus is detected through the photo detector 19.

The light reflected from the outside of the focal plane of the objective lens 15 is not passed through the aperture 17 and thus not detected through the photo detector 19, so that the confocal microscope has a high resolution limit in the direction of an optical axis thereof and further has a higher resolution limit in a vertical direction with respect to the optical axis than the existing optical microscope.

Further, the image can be obtained through optical sectioning using the laser light source, without mechanical cutting of the sample, so that the confocal microscope can observe a given plane of the sample, obtain the three-dimensional image of the sample, perform various image processing, observe the variations of ions and pH for live materials, and analyze the correlation between the materials within cells using the properties of the fluorescent material.

Such confocal optical system having high resolution limit and three-dimensional image acquiring performance has been recently adopted in a variety of professional fields such as cell biology, semiconductor chip inspection, and large optical lens or mirror used for artificial satellite of aerospace industry, and further, the confocal optical system has been widely applied to inspect the quality of semiconductor display parts, automobile parts, portable camera and copier parts over a variety of fields closely related to living.

According to the above-mentioned confocal microscope, on the other hand, the laser light irradiated from the light source 11 is focused to form the image on the surface of the sample through the microlens as the objective lens 15 located on the lower portion of the confocal microscope, and as shown in FIG. 2, the light L is incident into the microlens 15 in a form of parallel light, focused through the spherical shape of the microlens 15, and irradiated to the surface of the sample.

According to the confocal optical system, however, the focal length of the light incident to the form of parallel light and focused through the microlens 15, that is, the focal length f of the microlens 15 is very short, so that the working distance W from the surface of the sample to the microlens 15 is not sufficiently ensured upon the measurement of the sample, thus undesirably making the optical system and the surface of the sample brought into contact with each other. Specifically, as shown in FIG. 3, if the surface S of the sample 20 is irregular and bent, the microlens 15 located on the lower portion of the optical system and the surface S of the sample 20 are brought into contact with each other in the process of measuring the surface of the sample 20, thus making the microlens 15 or the surface S of the sample 20 contaminated or scratched.

So as to prevent the optical system and the surface S of the sample 20 from being brought into contact with each other, accordingly, a separate stage is adopted to convey the optical system or the sample in a direction of an axis z, but in this case, a high degree of precision should be needed to control the optical system in the direction of the axis z. Furthermore, the formation of the separate stage makes the whole configuration of the system undesirably complicated.

In scanning the surface of the sample using the conventional confocal optical system, further, so as to locate a single beam spot or optical probe over the whole area to be measured on the surface of the sample, as shown in FIG. 4, an actuator should be used to finely move the nano stage on which the sample is mounted.

However, a long period of time is needed to move the single beam spot over the area to be measured, and further, the whole performance of the optical system is lowered due to the vibrations generated by the activation of the actuator.

So as to solve the above-mentioned problems, as shown in FIG. 5, an optical system having multiple optical probes is provided wherein a plurality of beam spots or optical probes are irradiated at the same time, so that the information corresponding to the number of beam spots is obtained by the unit of page through the photo detector.

Referring to FIG. 6 showing the optical system having multiple optical probes, in acquiring the surface information over the whole measuring area (that is, the area indicated by the dash-dot line of FIG. 6), advantageously, each beam spot is moved only within the area (macrocell, which means the area of x0 and y0 of FIG. 6) reduced in inverse proportion to the number of beam spots.

When compared with the existing single beam spot, the moving line of each beam spot is further shortened, but the optical system having multiple optical probes still needs a long period of time for moving the beam spots over a two-dimensional area in a longitudinal direction (in the direction of y) thereof and in a traverse direction (in the direction of x) thereof by given step. That is, if scanning within the multiple optical probe arrangement area (unit) being currently measured is finished, the multiple optical probes should be moved to the area adjacent to the scanned area and stop there, and after that, the beam spots should be moved in the longitudinal direction and in the traverse direction by given step. The processes are repeatedly carried out.

As the size of the measuring object becomes large, recently, it is hard to measure a large area with a high resolution limit, and according to the conventional optical system having the multiple optical probes, the movements of the beam spots for filling the surface of the sample and the movements and stop of the beam spots to the unit positions of the multiple optical probes are repeatedly conducted one by one to achieve the measurement of the surface of the sample, thus needing a substantially long period of time for measuring the large area and lowering the efficiency of quality inspection.

DISCLOSURE

Technical Problem

Accordingly, the present invention has been made in view of the above-mentioned problems occurring in the prior art, and it is an object of the present invention to provide a multiple parallel confocal system and a surface measurement method using the same that can allow a working distance between microlenses and a measuring object to be extended to reduce the formation of contamination and scratches on the surfaces of the microlenses and the measuring object and that can scan the surface of the measuring object more rapidly over the area of the multiple optical probe as well as a large area exceeding the area of the multiple optical probe.

Technical Solution

To accomplish the above object, according to the present invention, there is provided a multiple parallel confocal system including: a light source for irradiating light; a relay lens unit through which the light traveling toward a measuring object or the light reflected from the measuring object is passed, the relay lens unit having one or more lens for focusing the light irradiated from the light source; a multiple optical probe having a microlens array on which a plurality of microlenses is arranged, the microlenses into which the focused light through the relay lens unit is incident; and a photo detector for detecting the incident light reflected from the measuring object and passed through the microlenses and the relay lens unit, wherein a working distance between each microlens and the measuring object is increased, a back focus determined by the focal distance of each microlens and the working distance between the microlens and the measuring object and a focus of the relay lens unit are located on the same plane, the back focus being calculated by the following expression: $BFL = f(f+x)/x$ (wherein f denotes the focal distance of each microlens and f+x denotes the distance between each microlens and the measuring object), and an aperture is disposed on a focal plane where the focuses of the relay lens unit and the back focuses of the microlenses meet, the aperture having pinholes formed thereon.

According to the present invention, desirably, the relay lens unit includes the aperture.

According to the present invention, desirably, the relay lens unit includes a telecentric lens.

According to the present invention, desirably, the light source is disposed above the optical axis of the telecentric lens.

According to the present invention, desirably, the light source is disposed under the optical axis of the telecentric lens.

According to the present invention, desirably, the multiple parallel confocal system further includes a beam splitter adapted to convert the advancing paths of the light irradiated from the light source.

According to the present invention, desirably, the multiple optical probe having the microlens array includes: a first column along which the microlenses are arranged in the traverse direction thereof; and a second column along which the microlenses are arranged in the longitudinal direction with respect to the first column in such a manner as to allow a portion of each microlens to be located between the neighboring microlenses of the first column.

According to the present invention, desirably, the distance between the neighboring microlenses of the second column is the same as that of the first column in such a manner as to be located traversely with respect to the first column.

According to the present invention, desirably, the distance between the neighboring microlenses of the second column is different from that of the first column.

According to the present invention, desirably, the first column has a given distance shorter than the distance between the neighboring microlenses thereof, and the microlenses of the second column are partially protruded toward the distance between the neighboring microlenses of the first column or completely traverse the distance between the neighboring microlenses of the first column.

According to the present invention, desirably, the multiple optical probe having the microlens array further comprises a third column along which the microlenses are arranged in the longitudinal direction with respect to the first and second columns in such a manner as to be partially located between the microlenses of the first and second columns.

Advantageous Effects

As described above, the multiple parallel confocal microscope system allows the working distance between the microlenses and the measuring object to be extended to reduce the formation of the contamination and scratches on the surfaces of the microlenses and the measuring object, and further, the optical pinhole effect can be obtained using the optical paths of the relay lens unit, without any having a physical pinhole.

Furthermore, under the microlens array structure wherein the microlenses in one column are located between the distance between the microlenses in another column, the multiple optical probe or the measuring object is moved continuously in the longitudinal direction (single direction) thereof, so that the measuring object can be scanned over the rectangular area or linear area thereof corresponding to the traverse width of the microlenses constituting the columns.

In scanning the unit area of the multiple optical probe, additionally, unlike the conventional practice wherein the beam spots are moved longitudinally and traversely over the two-dimensional area designated in the unit of beam spot, the present invention can scan the unit area of the multiple optical probe rapidly by the continuous movement of the multiple optical probe in the single direction.

In scanning the large area exceeding the unit area of the multiple optical probe, further, unlike the existing optical system wherein the movements of the beam spots for filling the surface and the movements and stop of the beam spots to the unit position of the multiple optical probe are repeatedly conducted one by one, the present invention can scan the unit area of the multiple optical probe rapidly by the continuous movement of the multiple optical probe in the single direction.

MODE FOR INVENTION

An optical system (for example, a confocal microscope, a confocal sensor and so on) having multiple optical probes is applicable to various embodiments in accordance with the selection, combination, shape, installation structure and number of optical components based on the purpose of use thereof.

The present invention relates to a multiple optical probe widely applicable to such multiple probe optical system, and more particularly, to a structure wherein one or two or more components, which are selected from a surface-emitting layer for emitting a plurality of laser light, a confocal aperture where a plurality of pin holes is formed to pass the plurality of laser light transmitted to or reflected from a measuring object, a focusing microlens, a collimator lens, and a light receiving part of a photo detector like CCD, are combined to each other.

Hereinafter, an explanation on a multiple parallel confocal system according to the present invention will be in detail given with reference to the attached drawing.

Figure 7:
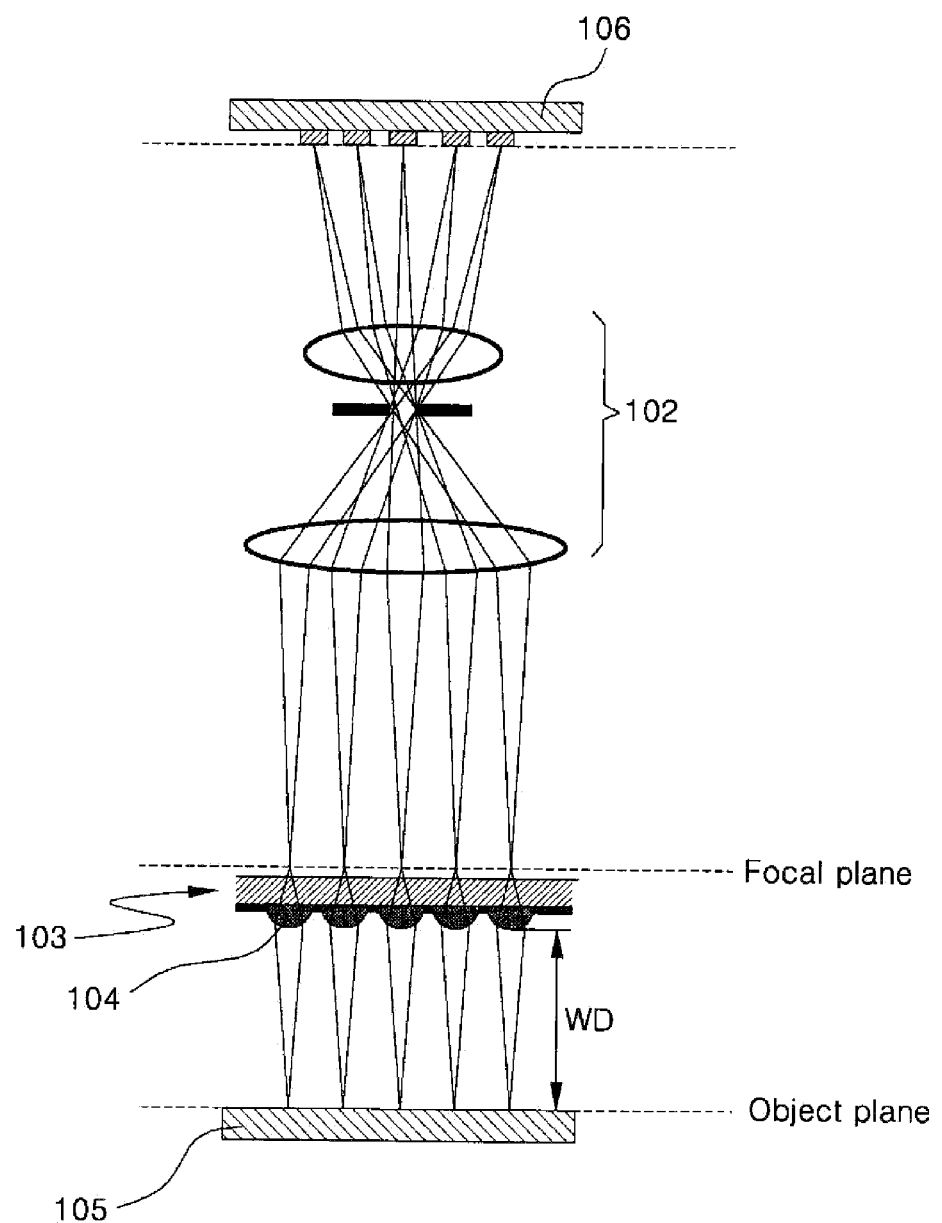
FIG. 7 is a concept view showing the configuration of a multiple parallel confocal system according to a first embodiment of the present invention.

FIG. 7 is a concept view showing the configuration of a multiple parallel confocal system according to a first embodiment of the present invention.

As shown in FIG. 7, a multiple parallel confocal system according to a first embodiment of the present invention includes: a light source (not shown) for irradiating light; a relay lens unit 102 through which the light traveling toward a measuring object 105 or the light reflected from the measuring object 105 is passed, the relay lens unit 102 having one or more lens for focusing the light irradiated from the light source; a multiple optical probe 103 having a microlens array on which a plurality of microlenses 104 is arranged, the microlenses 104 into which the focused light through the relay lens unit 102 is incident; and a photo detector 106 for detecting the incident light reflected from the measuring object 105 and passed through the microlenses 104 and the relay lens unit 102.

The relay lens unit 102 is an optical microscope for focusing the light incident into the microlenses 104 and includes a telecentric lens for compensating for the depth feeling according to the location of the surface of the measuring object 105 when the measuring object 105 is measured.

At this time, the telecentric lens may have two focusing lenses for focusing the light traveling toward the measuring object 105 or the light reflected from the measuring object 105 and an aperture disposed between the focusing lenses.

The relay lens unit 102 focuses the light incident into the light source to a form of focused light, not to a form of existing parallel light, and allows the focused light to be incident into the microlenses 104 of the multiple optical probe 103 located under the relay lens unit 102.

Figure 8:
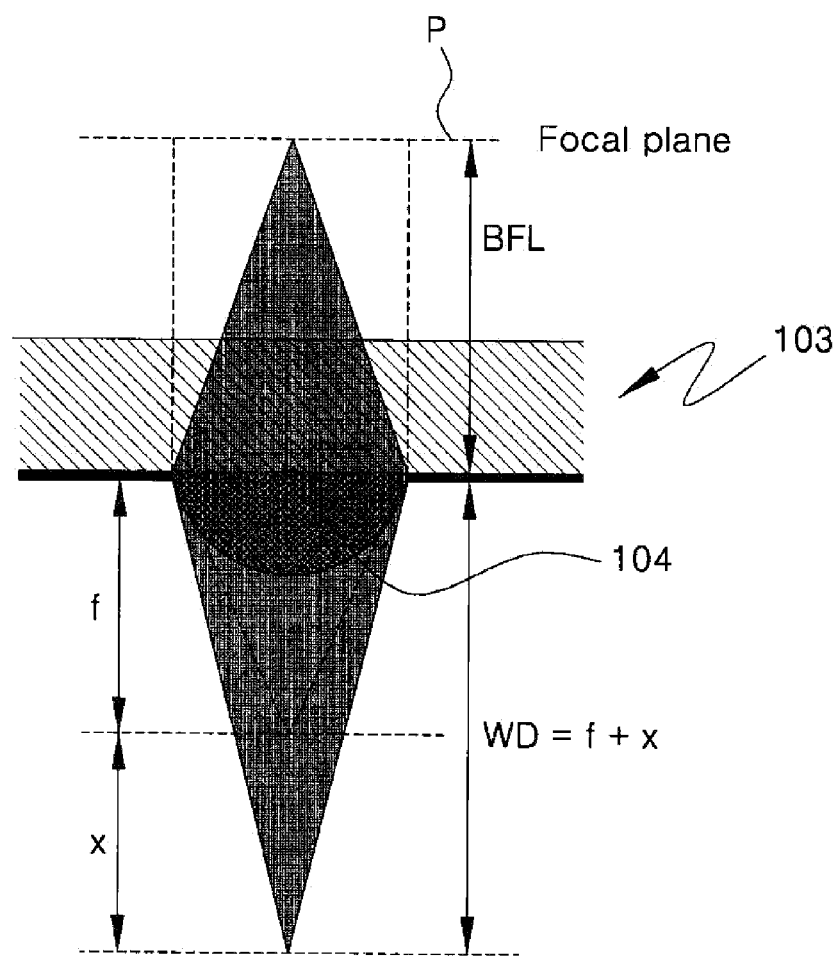
FIG. 8 is a sectional view showing each microlens of a multiple optical probe of the multiple parallel confocal system according to the first embodiment of the present invention.

FIG. 8 is a sectional view showing one microlens 104 formed on the microlens array of the multiple optical probe 103 of the multiple parallel confocal system according to the first embodiment of the present invention.

As shown in FIG. 8, the light focused through the relay lens unit 102 located over the microlens 104 is incident into the microlenses 104. In this case, a focus is formed at a working distance WD longer than the focal length f of the microlens 104 when the incidence is carried out in the form of existing parallel light (which means light paths indicated by dotted lines), and the light reflected from the surface of the measuring object 105 is passed through the microlens 104 again to form a focus behind the microlens 104.

At this time, a back focus determined by the focal length f of the microlens 104 and the working distance WD between the microlens 104 and the measuring object 105 and a focus of the relay lens unit 102 are located at the focal plane on the same plane, as shown in FIG. 7.

In this case, a length BFL of the back focus determined by the focal length f of the microlens 104 and the working distance WD between the microlens 104 and the measuring object 105 is calculated by the following expression when it is assumed that the focal length of the microlens 104 is f and the distance between the microlens 104 and the measuring object 105 is f+x.

$$BFL=f(f+x)/x$$

That is, if light is incident into the microlens 104 to the form of focused light by means of the relay lens unit 102, the working distance WD is formed by adding a distance x to the original focal length f, in front of the microlens 104.

In this case, the distance from the microlens 104 to the object plane is effectively longer than the focal length f of the microlens 104. Accordingly, the working distance from the microlens 104 to the measuring object 105 is extended so that the measuring object 105 can be scanned without having any influence on the bending states on the surface of the measuring object 105.

Figure 9:
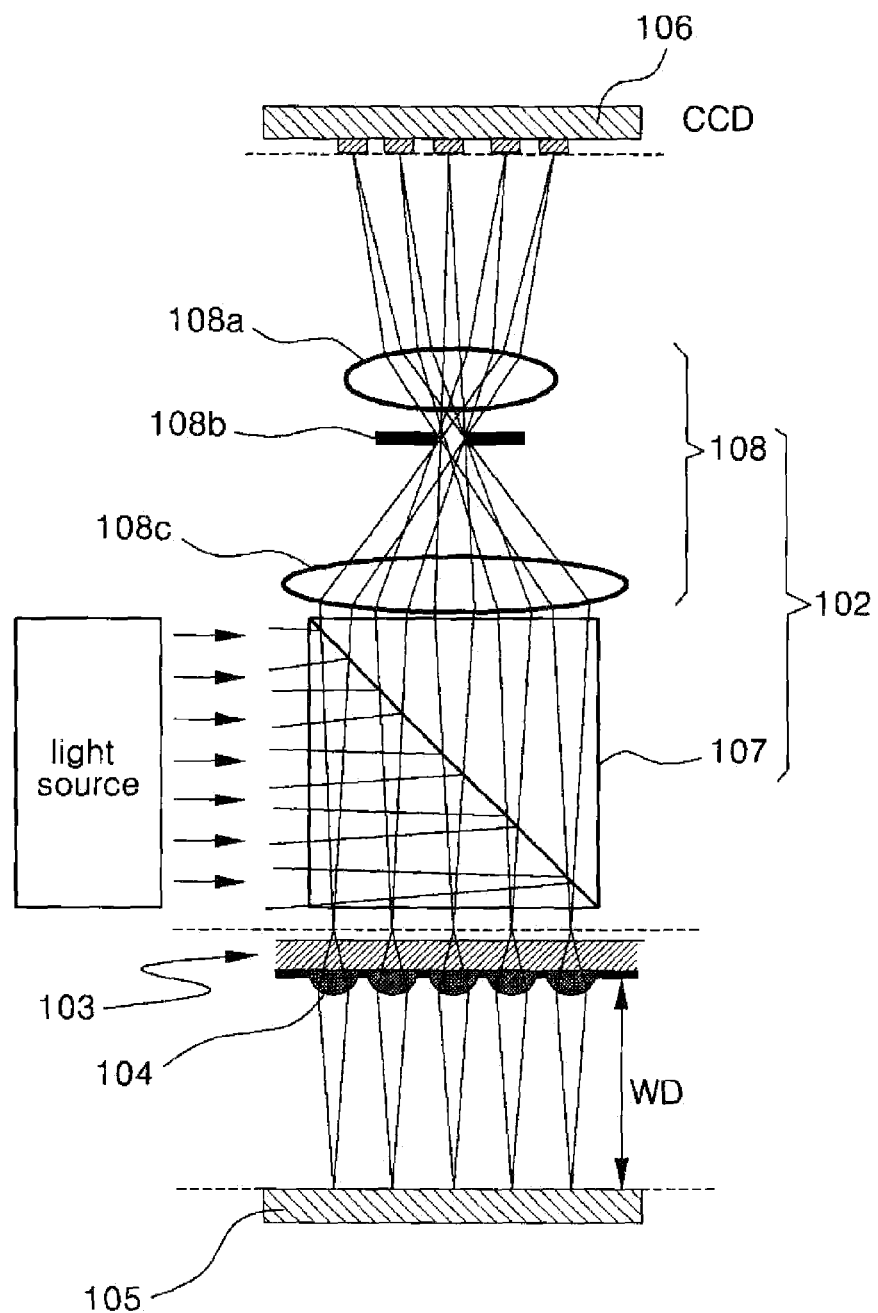
FIG. 9 is a concept view showing a multiple parallel confocal system according to a second embodiment of the present invention, wherein a relay lens unit includes a telecentric lens and a beam splitter.

FIG. 9 shows a multiple parallel confocal system according to a second embodiment of the present invention, wherein the relay lens unit has a telecentric lens and a beam splitter.

As shown in FIG. 9, the relay lens unit 102 as the optical microscope for focusing the light includes: a telecentric lens 108 having two focusing lenses 108a and 108c and an aperture 108b disposed between the focusing lenses 108a and 108c; and a beam splitter 107 disposed under the optical axis of the telecentric lens 108 so as to convert the advancing paths of light irradiated from the light source.

At this time, as shown in FIG. 9, the light source is disposed under the optical axis of the telecentric lens 108, and alternatively, it is disposed above the optical axis of the telecentric lens 108. In this case, if the light source is disposed above the optical axis of the telecentric lens 108, the beam splitter 107 is disposed above the telecentric lens 108.

Figure 10:
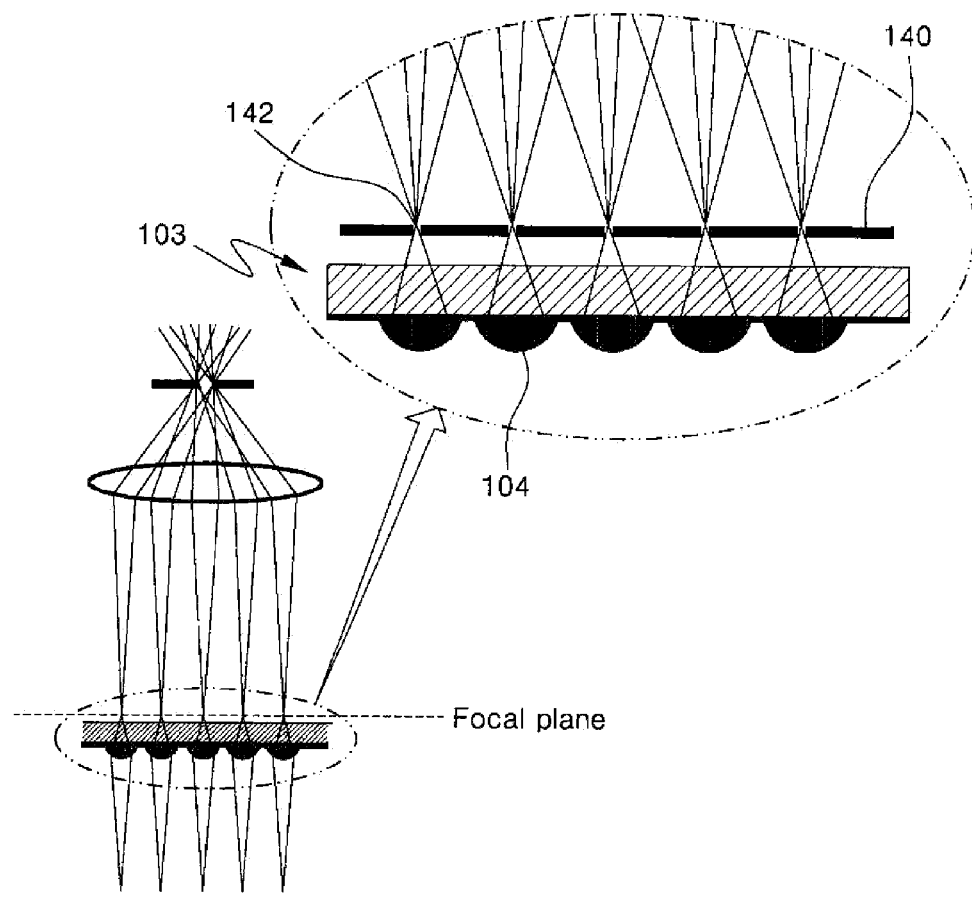
FIG. 10 is a concept view showing a multiple parallel confocal system according to a third embodiment of the present invention, wherein an aperture having pin holes formed thereon is additionally disposed on a focal plane where focuses of a relay lens unit and microlenses meet.

On the other hand, FIG. 10 shows a multiple parallel confocal system according to a third embodiment of the present invention, wherein an aperture 140 having pin holes 142 formed thereon is additionally disposed on a focal plane where the focuses of the relay lens unit 102 and the back focuses of the microlenses 104 meet.

Figure 11:
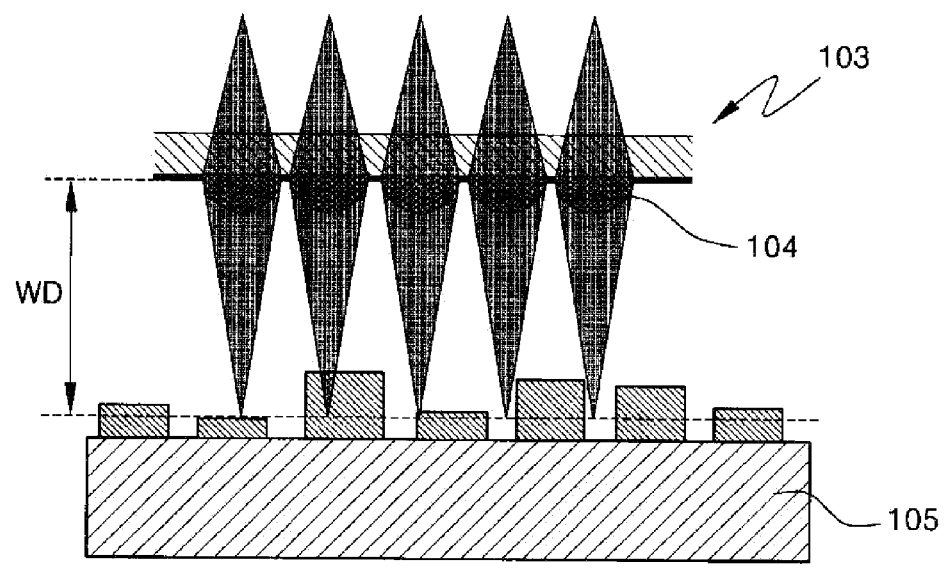
FIG. 11 is a concept view showing the checking state of the surface of a measuring object using the confocal system having an improved working distance according to the present invention.

FIG. 11 is a concept view showing the checking state of the surface of the measuring object using the confocal system according to the present invention. As shown in FIG. 11, if the measuring object 105 is measured by using the confocal system according to the present invention which has the working distance WD longer than the existing focal length f of the microlens, the surface of the measuring object 105 can be scanned without any contact with the microlenses 104, thus preventing the surfaces of the microlenses 104 and the measuring object 105 from being contaminated or scratched due to the contact therebetween. Furthermore, the existing confocal system needs a separate device for conveying the confocal system or the measuring object to a direction of an axis Z so as to avoid the contact therebetween, but the confocal system according to the present invention does not need such separate device, thus allowing the configuration of the whole system to be simplified and compact.

Figure 12:
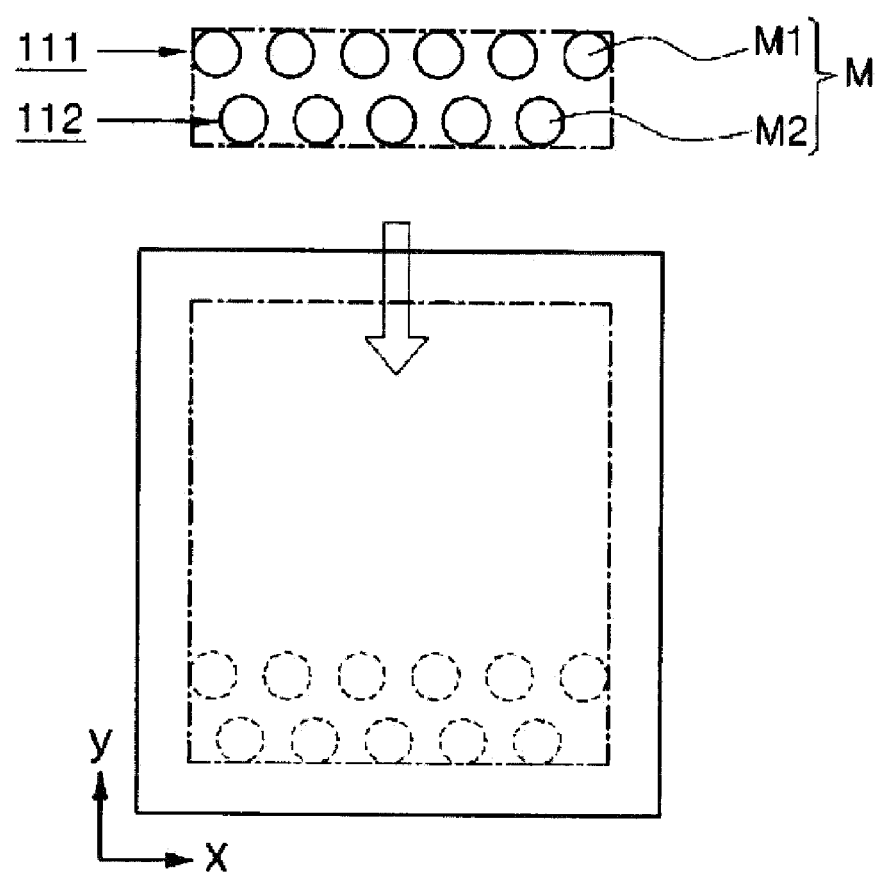
FIG. 12 is a concept view showing a scanning method using the microlens array of a multiple optical probe according to the present invention.

On the other hand, FIG. 12 is a concept view showing a scanning method using the microlens array of the multiple optical probe according to the present invention, and FIGS. 13 to 21 are concept views showing various microlens array structures of the multiple optical probe and the scanning areas thereof.

FIGS. 13 to 21 show first to tenth microlens array structures, which show the microlens arrays of the multiple optical probe in the confocal system of the present invention and at the same time the arrangements of the beam spots which reach the surface of the measuring object after passing through the plurality of microlenses M constituting the microlens array.

Referring to FIGS. 13 to 21, the multiple optical probe in the confocal system of the present invention includes: a microlens array structure having a first column 111 along which microlenses M1 are arranged in a traverse direction (in a direction of x); and a second column 112 along which microlenses M2 are arranged in a longitudinal direction (in a direction of y) with respect to the first column 111 in such a manner as to allow a portion of each microlens M2 to be located between the neighboring microlenses M1 of the first column 111.

Accordingly, the microlenses M2 of the second column 112 are partially protruded toward the distance between the neighboring microlenses M1 of the first column ill or completely traverse the distance between the neighboring microlenses M1 of the first column 111.

Figure 1:
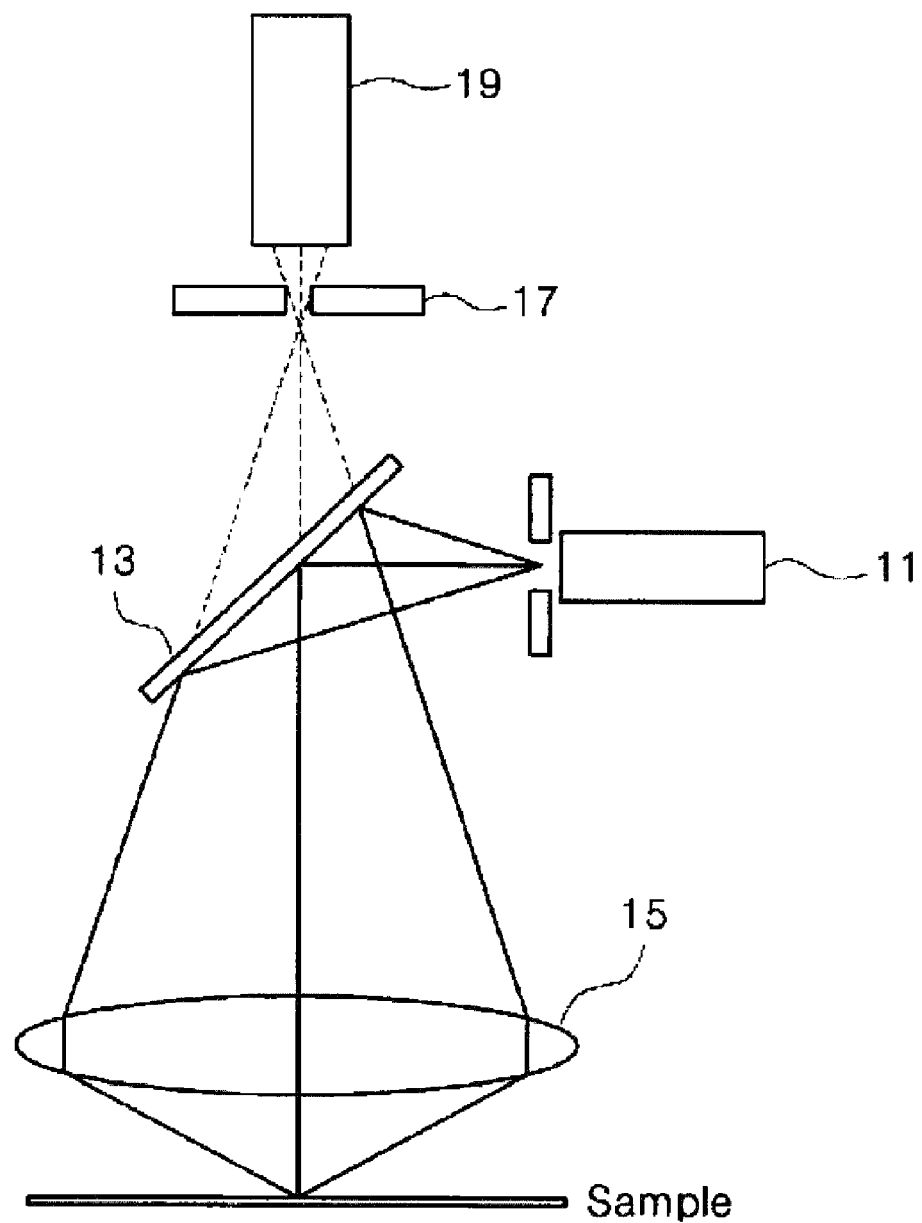
FIG. 1 is a concept view showing a confocal optical system to which the principle of a general confocal microscope is applied.
Figure 2:
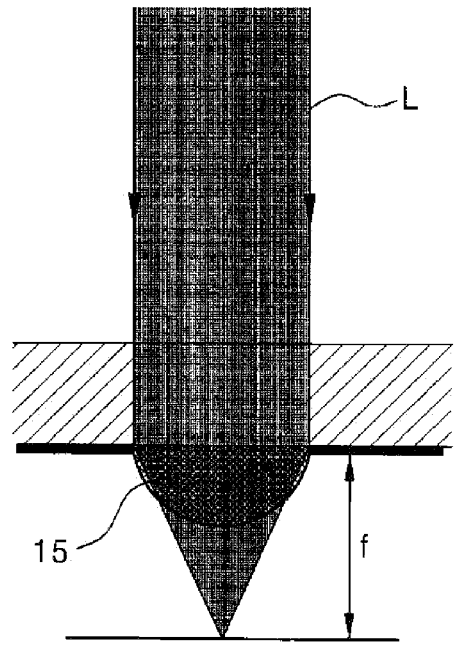
FIG. 2 is a sectional view showing the main part of a conventional confocal optical system.
Figure 3:
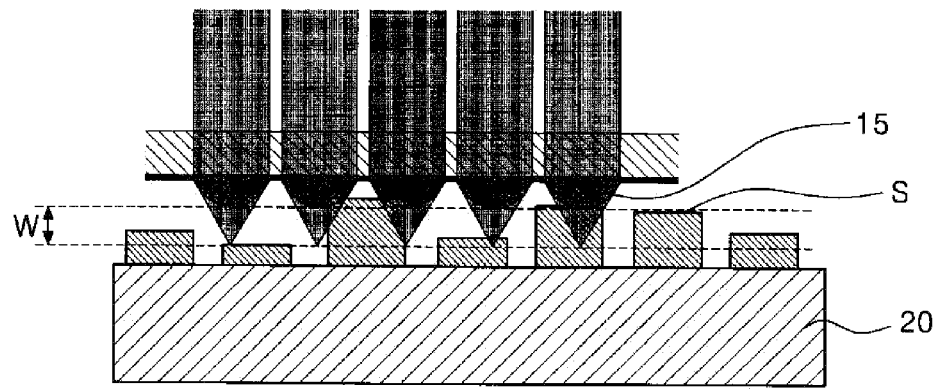
FIG. 3 is a concept view showing the measurement state of a measuring object using the conventional confocal optical system.
Figure 4:
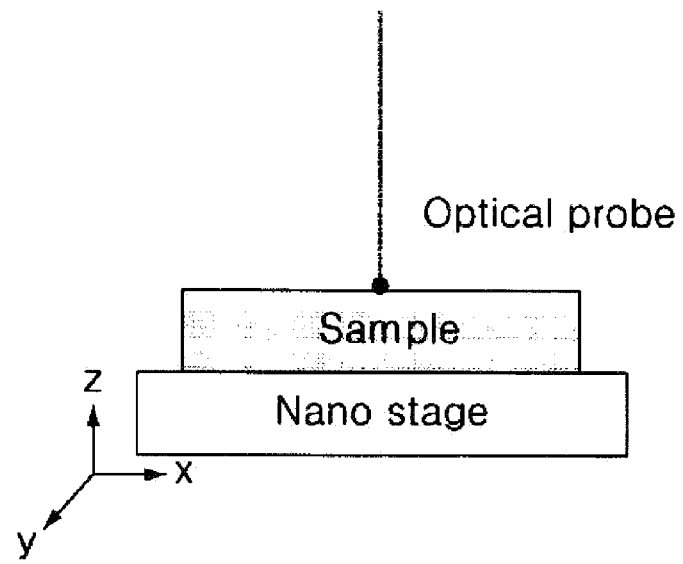
FIG. 4 is a concept view showing a scanning method using a single optical probe.
Figure 5:
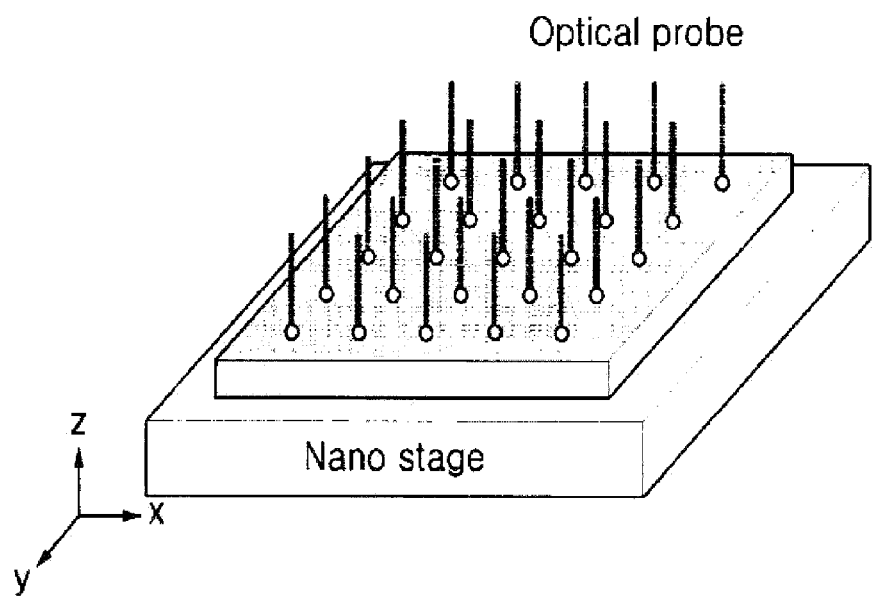
FIG. 5 is a concept view showing a scanning method using multiple optical probes.
Figure 6:
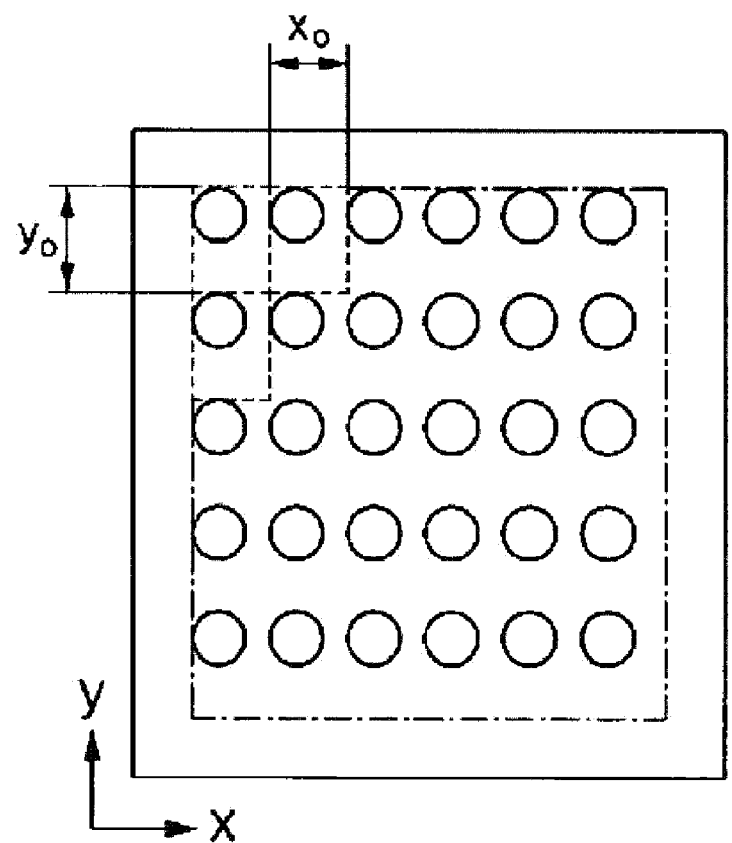
FIG. 6 is a concept view showing a scanning area formed by the multiple optical probes of FIG. 5.
Figure 13:
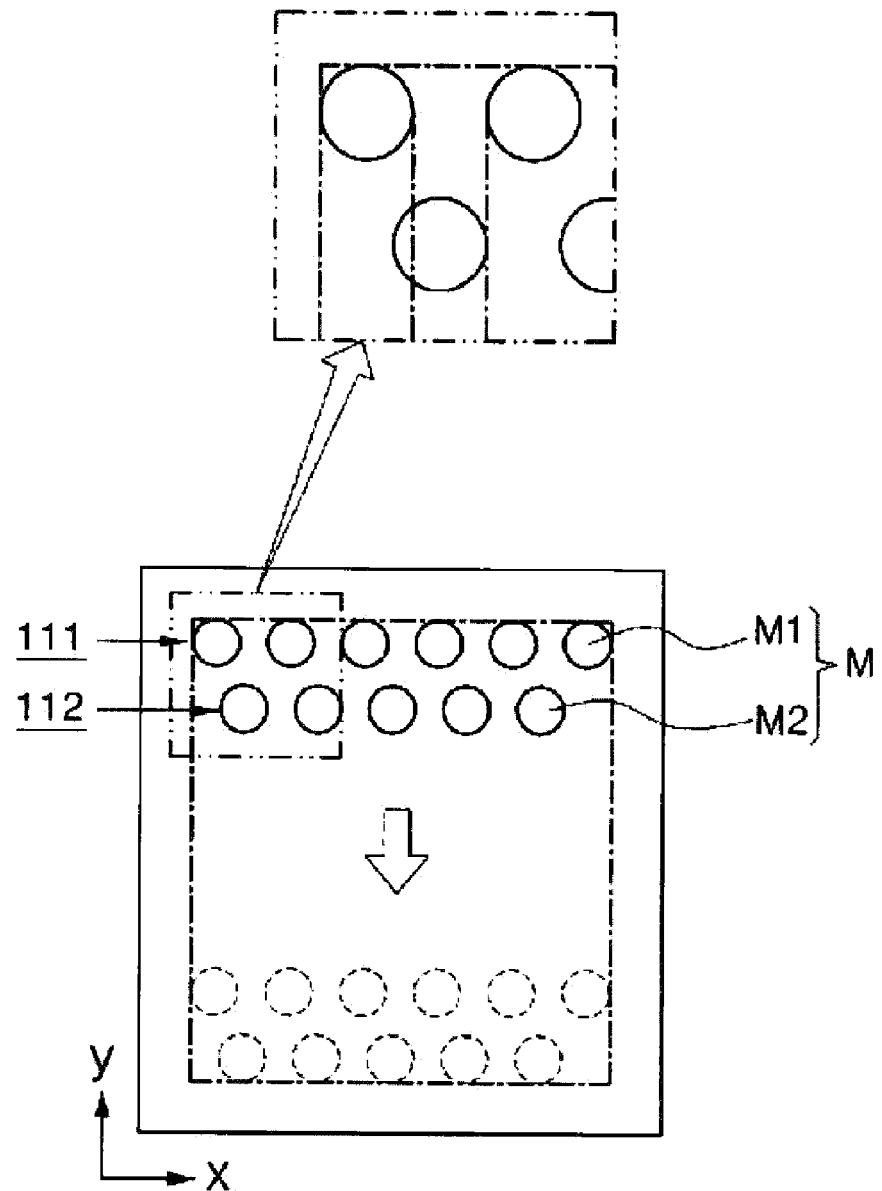
FIG. 13 is a concept view showing the microlens array of the multiple optical probe and the scanning area thereof according to a first microlens array structure of the present invention.

Referring to FIG. 13, the multiple optical probe has a first microlens array structure of the present invention wherein the first column 111 and the second column 112 are formed within the area indicated by the dash-dot line having the same size as the area (the unit area of the multiple optical probe) indicated by the dash-dot line in the conventional practice as shown in FIG. 6.

Compared with the conventional practice as shown in FIG. 6, the first column 111 has the same microlens arrangement as the uppermost column of the microlens array as shown in FIG. 6, and the second column 112 has the same distance between the microlenses M2 as the first column 111 in such a manner as to be located traversely with respect to the first column 111.

If the traverse distance between the beam spots through the microlenses M1 and M2 of the first and second columns 111 and 112 is shorter than the sizes of the beam spots, as shown in FIG. 13, the left or right end portion of the beam spot of the second column 112 in the traverse direction is located to completely fill the distance between the beam spots of the first column 111. In this case, as shown in FIG. 13, as the multiple optical probe according to the first microlens array structure is continuously moved in a longitudinal direction (in the direction of an arrow), the whole area indicated by the dash-dot line can be scanned at a high speed.

Under the conventional practice as shown in FIG. 6, the multiple optical probe has an arrangement of 6×5 so as to scan the whole area indicated by the dash-dot line, so that the beam spots should be moved longitudinally and transversely over the two-dimensional area (indicated by the dotted line) designated in the unit of beam spot. According to the first microlens array structure of the present invention, however, the multiple optical probe has a simple arrangement of 5~6×2 so that the whole area indicated by the dash-dot line can be easily scanned rapidly just by the continuous movement of the multiple optical probe or the measuring object in the longitudinal direction (single direction).

Figure 14:
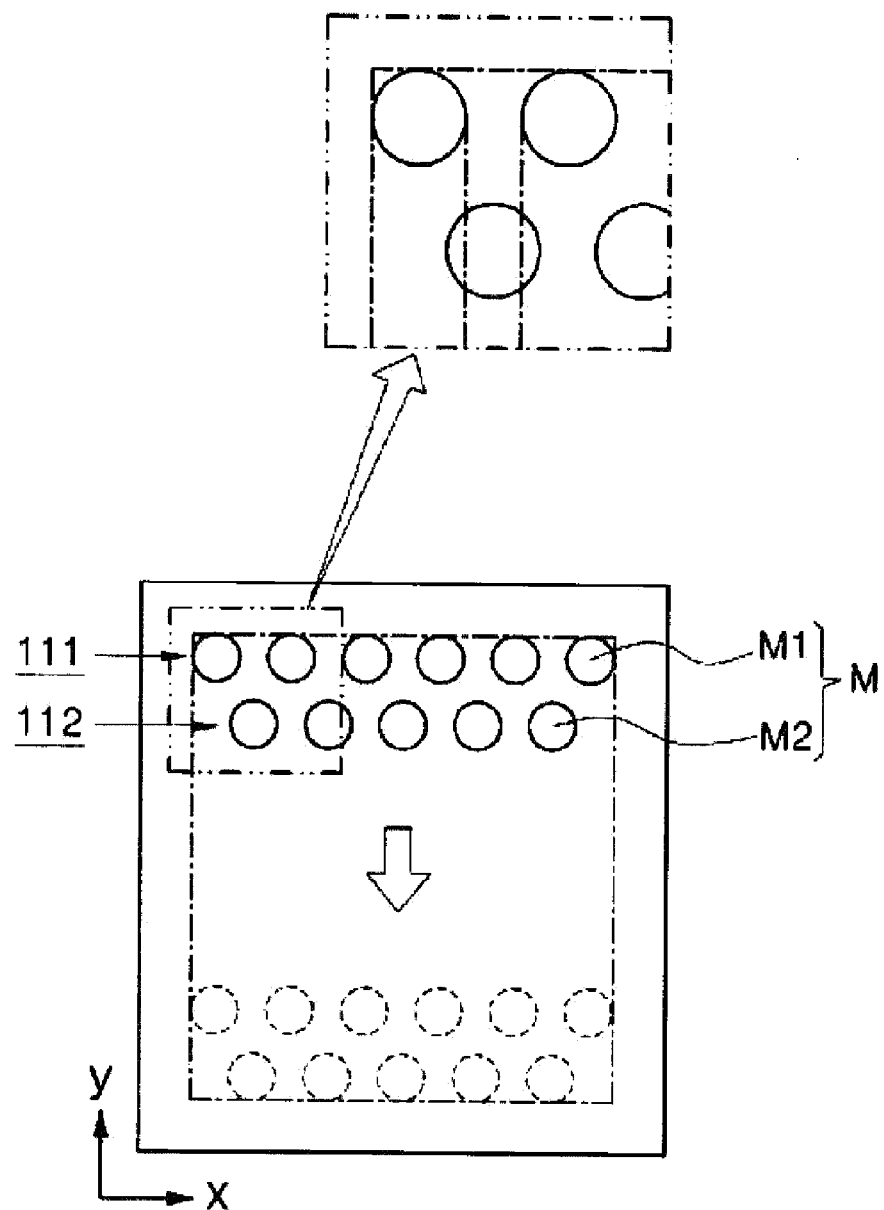
FIG. 14 is a concept view showing the microlens array of the multiple optical probe and the scanning area thereof according to a second microlens array structure of the present invention.

Referring to FIG. 14, the multiple optical probe has the second microlens array structure of the present invention wherein the intermediate portion in the traverse direction of the beam spot of the second column 112 is located to fill the entire distance between the neighboring beam spots of the first column 111.

The multiple optical probe according to the second microlens array structure of the present invention has more equally distributed microlens array than that according to the first microlens array structure of the present invention, and in the same manner as the first lens array of the present invention, as shown in FIG. 14, as the multiple optical probe according to the second microlens array structure of the present invention is continuously moved in a longitudinal direction (in the direction of an arrow), so that the whole area indicated by the dash-dot line can be scanned at a high speed.

Figure 15:
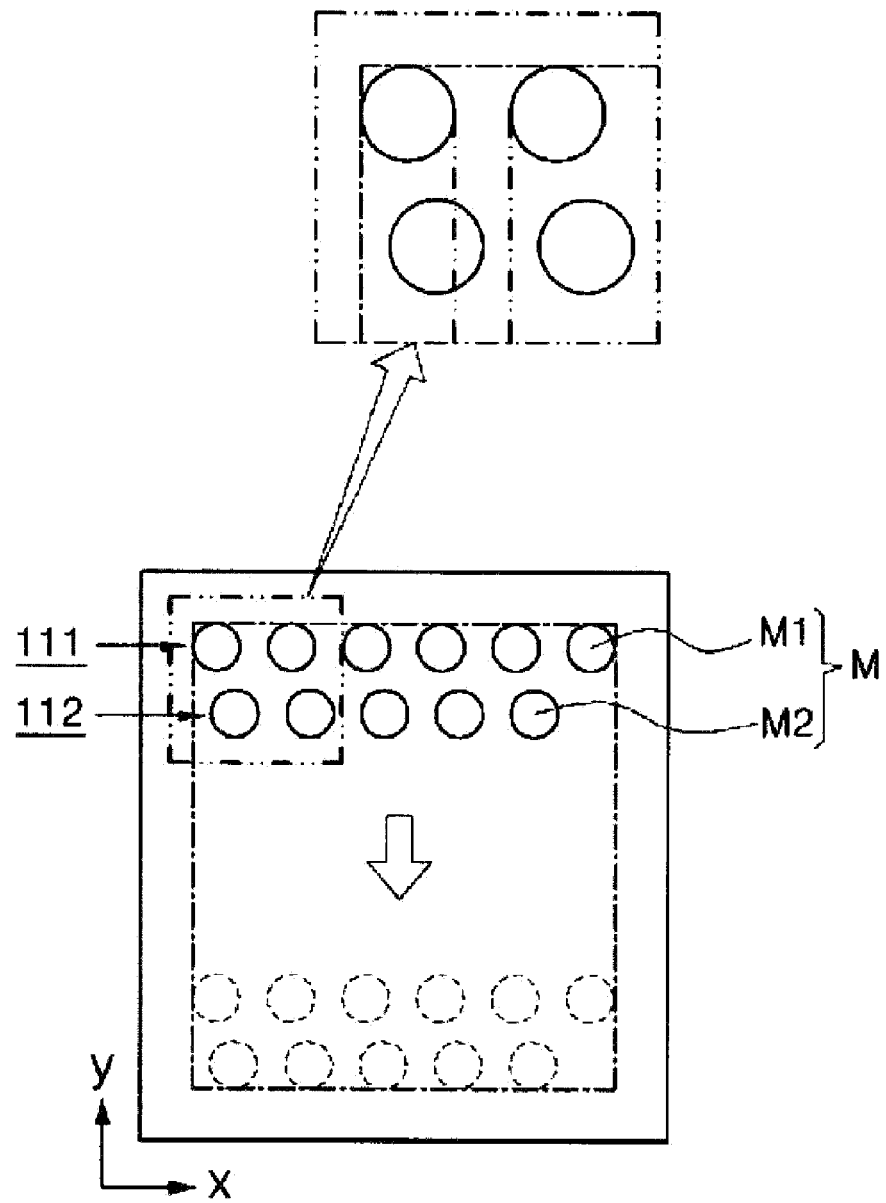
FIG. 15 is a concept view showing the microlens array of the multiple optical probe and the scanning area thereof according to a third microlens array structure of the present invention.

Referring to FIG. 15, the multiple optical probe has the third microlens array structure of the present invention wherein the left or right end portion in the traverse direction of the beam spot of the second column 112 is located to fill only a portion of the distance between the neighboring beam spots of the first column 111.

According to the third microlens array structure of the present invention, as shown in FIG. 15, as the multiple optical probe according to the second microlens array structure of the present invention is continuously moved in a longitudinal direction (in the direction of an arrow), a partial area having a shape of a stripe (continued in the longitudinal direction) having the width corresponding to the total width between the beam spots in the traverse direction of the microlenses M1 and M2 in the first and second columns 111 and 112 can be scanned at a high speed within the whole area indicated by the dash-dot line.

In scanning the whole area indicated by the dash-dot line by using the multiple optical probe according to the third microlens array structure of the present invention, the multiple optical probe according to the third microlens array structure of the present invention is continuously moved in a longitudinal direction (in the direction of an arrow), and next, it is moved in the traverse direction to allow the beam spots to be located at the area where scanning is not carried out. After that, the multiple optical probe is continuously moved in the longitudinal direction (in the opposite direction to the arrow).

Figure 16:
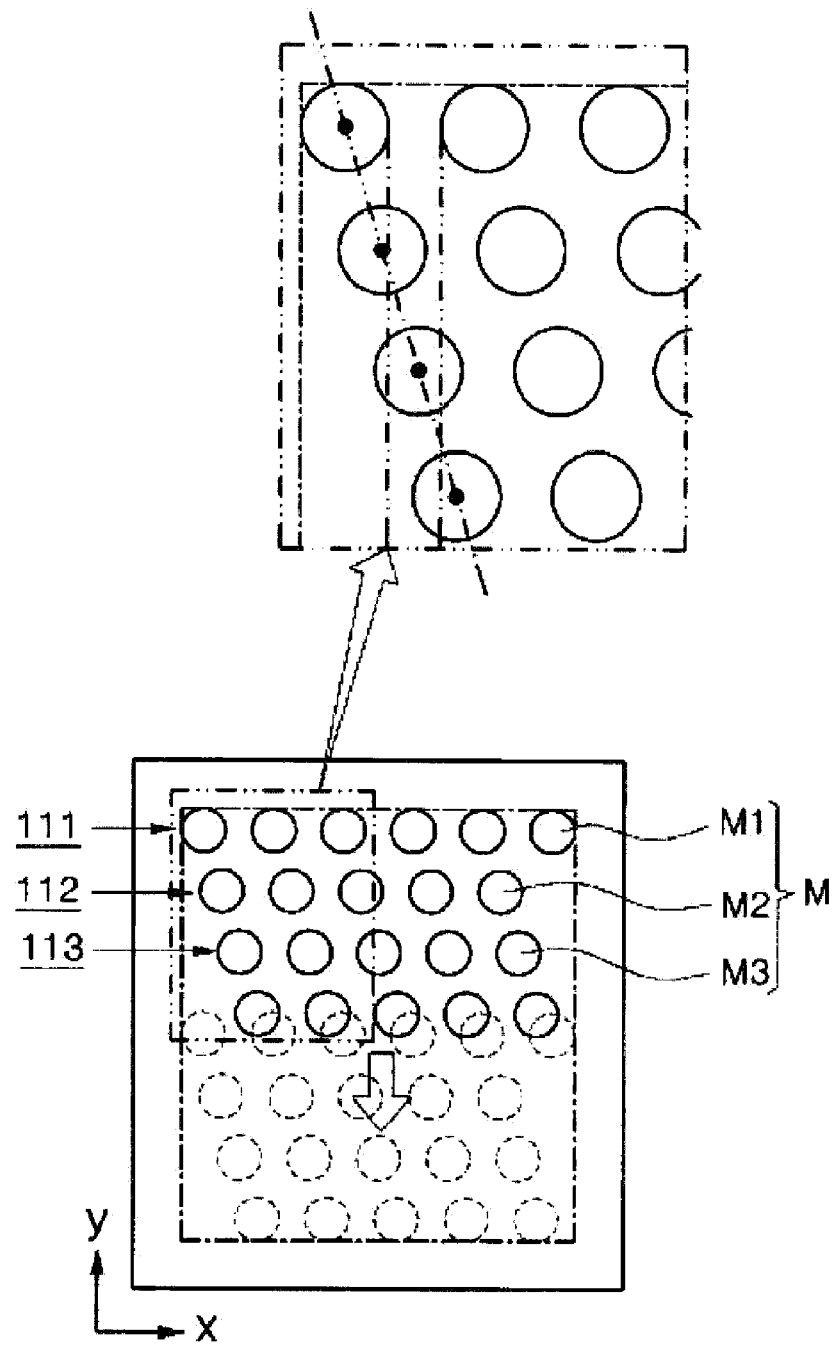
FIG. 16 is a concept view showing the microlens array of the multiple optical probe and the scanning area thereof according to a fourth microlens array structure of the present invention.

Referring to FIG. 16, the multiple optical probe has the fourth microlens array structure of the present invention wherein one or more columns inclusive of a third column 113 are formed, and the third column 113 has microlenses M3 arranged longitudinally with respect to the first and second columns 111 and 112 in such a manner as to allow a portion of each microlens M3 to be located between the microlenses M1 and M2 of the first and second columns 111 and 112.

The microlenses M3 of the third column 113 and another column are formed protrudedly from the distances between the microlenses M1 and M2 of the first and second columns 111 and 112 or formed traversely through the distances therebetween.

The multiple optical probe according to the fourth microlens array structure of the present invention further has the third column 113 and the fourth column, and when compared with the third microlens array structure wherein only a portion within the area indicated by the dash-dot line is scanned, accordingly, the multiple optical probe according to the fourth microlens array structure of the present invention can easily scan the whole area indicated by the dash-dot line rapidly by the continuous movement of the multiple optical probe or the measuring object in the longitudinal direction (single direction).

So as to provide the microlens array structure having a plurality of columns, for example, around the microlens M1 located at the leftmost end of the first column 111 as shown in FIG. 16, the microlenses located at the leftmost ends of the second column 112, the third column 113, and the fourth column are arranged to have the same traverse phase difference as each other, as indicated by the inclined dash-dot line in FIG. 16, thus achieving the uniform distribution of the microlenses.

So as to allow the microlenses in the second column 112, the third column 113, and the fourth column to have the same traverse phase difference as each other, accordingly, the leftmost microlenses of the second column 112, the third column 113, and the fourth column are located between the center points of the microlens M1 located at the leftmost end of the first column 111 and the neighboring microlens M1.

The microlens M1 adjacent to the microlens M1 located at the leftmost end of the first column 111 is desirably located to have the same traverse distance as the leftmost microlens in the last column among the plurality of columns.

That is, if the distance between the center points of the neighboring microlenses M1 of the first column 111 is 5 and the microlens array is composed of five columns, the traverse phase difference between the neighboring columns is 1, thus achieving the uniform distribution of the microlenses.

Figure 17:
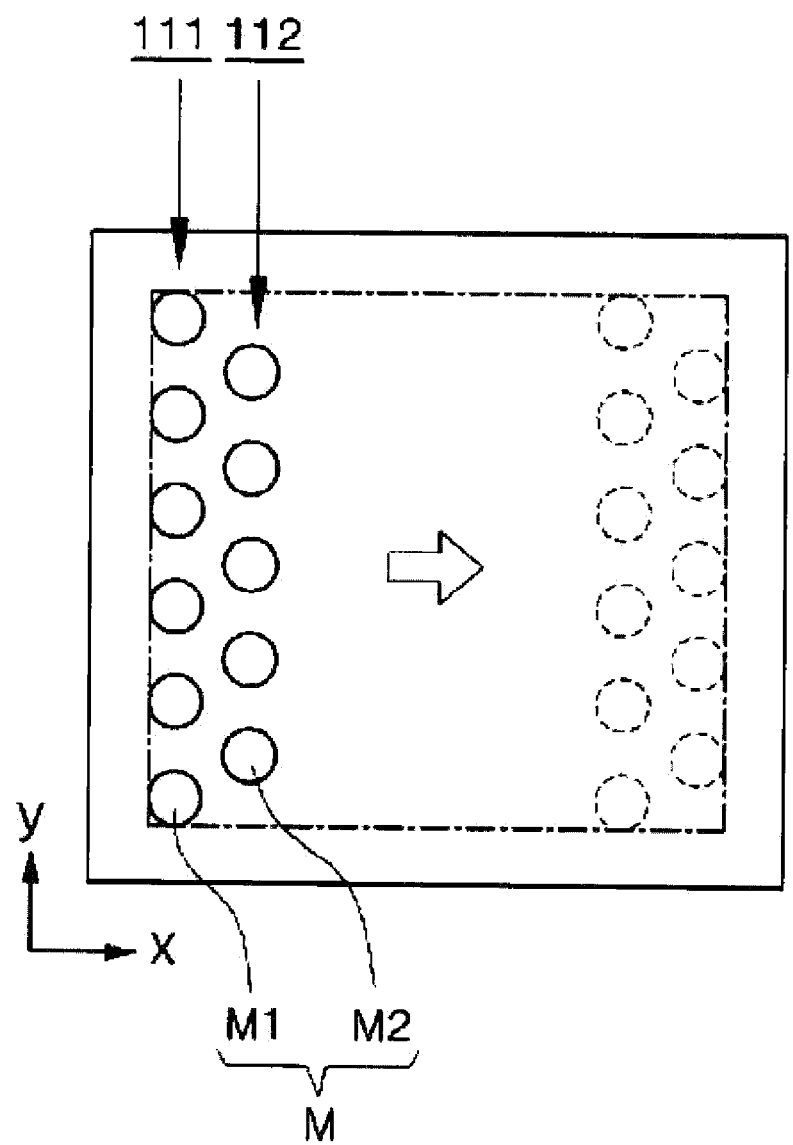
FIG. 17 is a concept view showing the microlens array of the multiple optical probe and the scanning area thereof according to a fifth microlens array structure.

Referring to FIG. 17, the multiple optical probe has the fifth microlens array structure of the present invention wherein the first and second columns 111 and 112 are located traversely on the microlens array, so that the whole area indicated by the dash-dot line can be easily scanned rapidly by the continuous movement of the multiple optical probe or the measuring object in the traverse direction (single direction).

Figure 18:
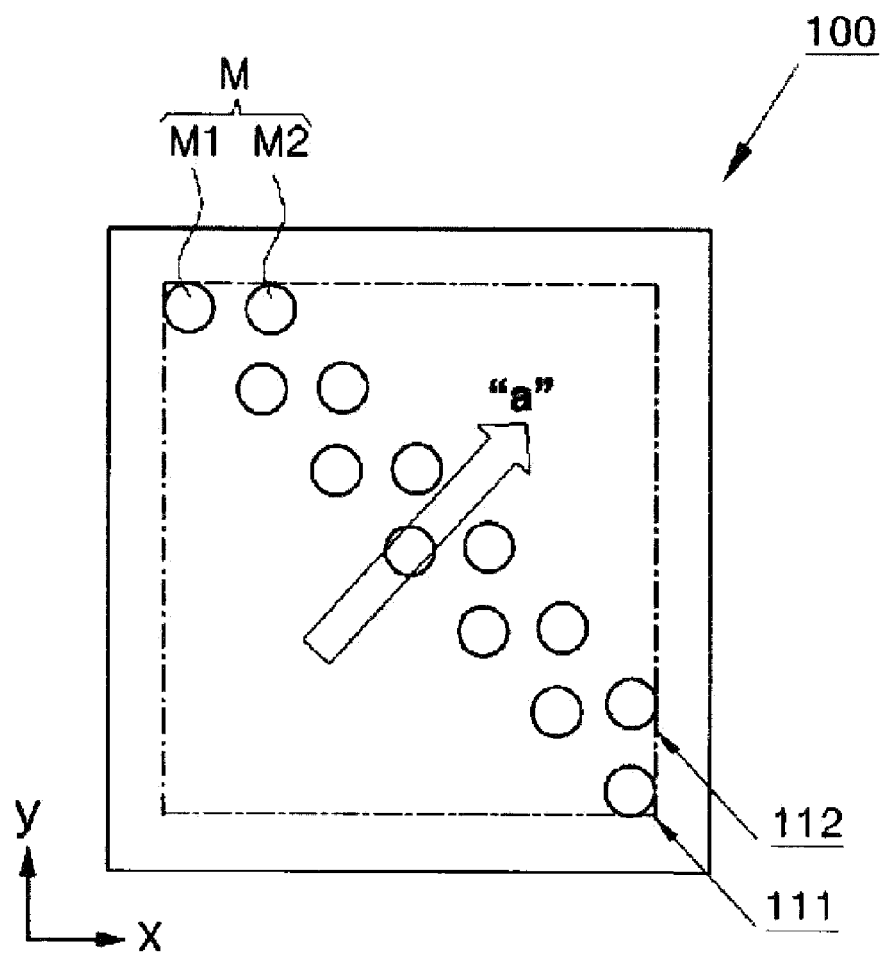
FIG. 18 is a concept view showing the microlens array of the multiple optical probe and the scanning area thereof according to a sixth microlens array structure of the present invention.

Referring to FIG. 18, the multiple optical probe has the sixth microlens array structure of the present invention wherein the first and second columns 111 and 112 are located along a slant line corresponding to an inclination 'a' on a linear equation 'y=ax+b', so that the whole area indicated by the dash-dot line can be easily scanned rapidly by the continuous movement of the multiple optical probe or the measuring object in the direction (single direction) of the inclination 'a'.

Figure 19:
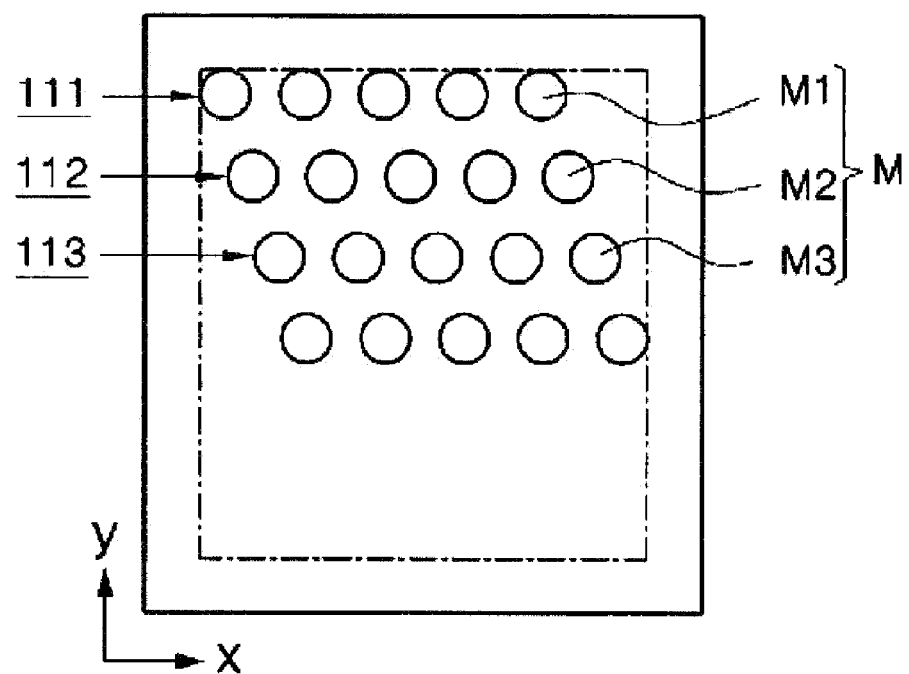
FIG. 19 is a concept view showing the microlens array of the multiple optical probe and the scanning area thereof according to a seventh microlens array structure of the present invention.

Referring to FIG. 19, the multiple optical probe has the seventh microlens array structure of the present invention wherein a plurality of columns inclusive of the first and second columns 111 and 112 are located within the area indicated by the dash-dot line and the number of microlenses M and the distance between the neighboring microlenses of each column are the same as each other.

Since the plurality of columns has the same arrangements as each other, the multiple optical probe can be made or the optical information using the multiple optical probe can be obtained not in the unit of individual microlenses, but in the unit of column.

Figure 20:
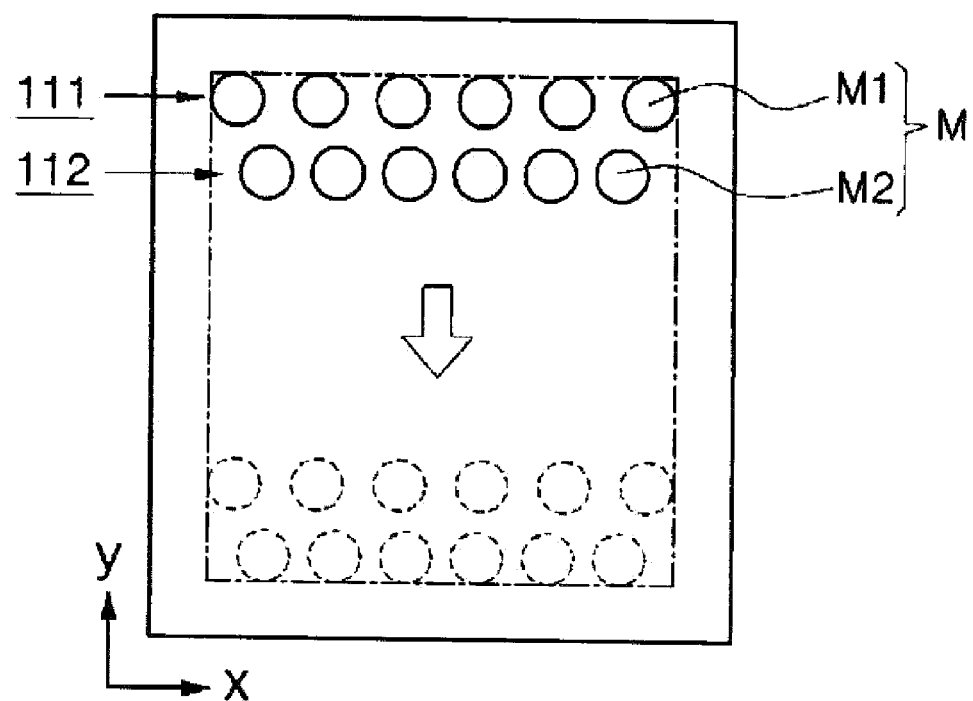
FIG. 20 is a concept view showing the microlens array of the multiple optical probe and the scanning area thereof according to an eighth microlens array structure of the present invention.

Referring to FIG. 20, the multiple optical probe has the eighth microlens array structure of the present invention wherein the distance between the neighboring microlenses M1 of the first column 111 is different from that between the neighboring microlenses M2 of the second column 112.

That is, the microlenses M2 in the second column 112 are located more tensely than those in the first column 111, and if the microlenses M1 of the first column ill are located more tensely than those of the second column 112, a plurality of columns inclusive of the second column 112 are formed in relatively less tense manner.

Figure 21:
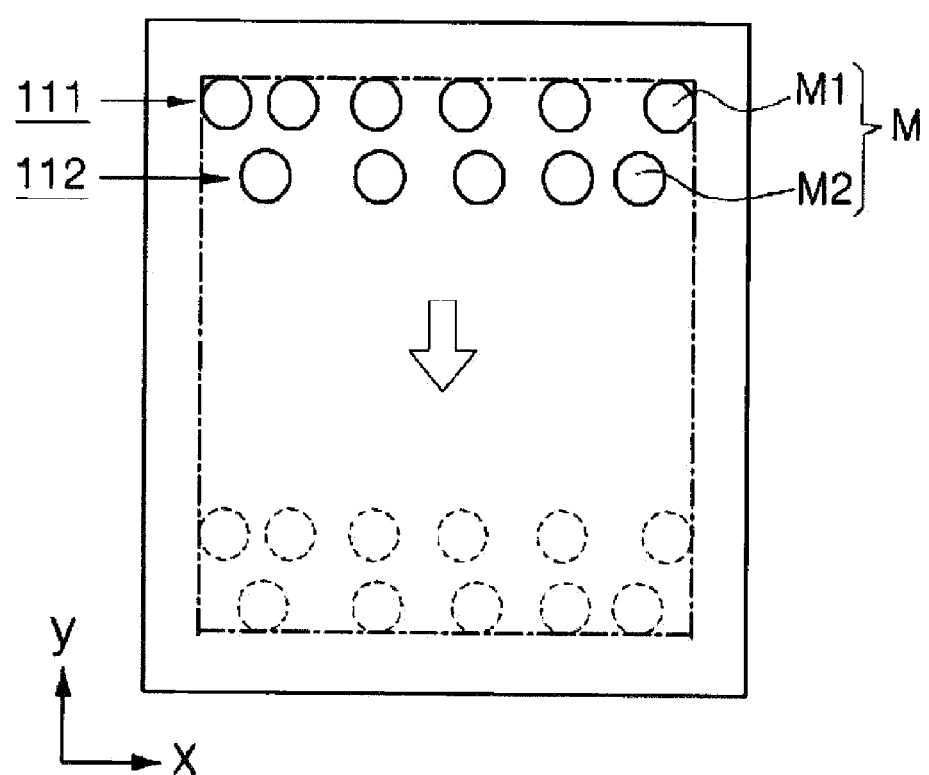
FIG. 21 is a concept view showing the microlens array of the multiple optical probe and the scanning area thereof according to a ninth microlens array structure of the present invention.

Referring to FIG. 21, the multiple optical probe has the ninth microlens array structure of the present invention wherein the distances between the neighboring microlenses M1 of the first column 111 are different from each other and the distances between the neighboring microlenses M2 of the second column 112 are different from each other.

As shown in FIG. 21, if the distances between the neighboring microlenses M1 of the first column 111 are gradually increased toward one side thereof in the traverse direction thereof, the distances between the neighboring microlenses M2 of the second column 112 located between the distances between the neighboring microlenses M1 of the first column 111 are gradually decreased toward one side thereof in the traverse direction thereof, so that the traverse width scannable through the microlenses M1 and M2 at the same time can be expanded to the maximum extent.

Figure 22:
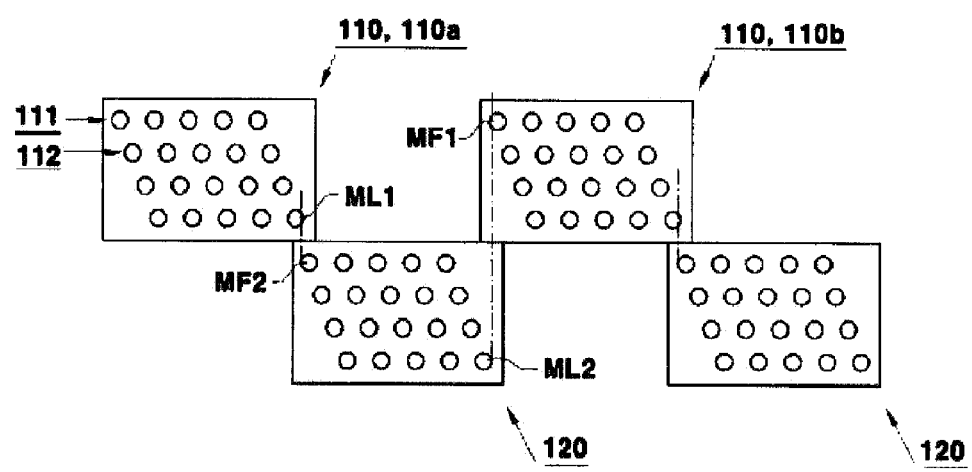
FIG. 22 is a concept view showing the microlens array of the multiple optical probe and the scanning area thereof according to a tenth microlens array structure of the present invention.

FIG. 22 is a concept view showing the microlens array of the multiple optical probe and the scanning area thereof according to a tenth microlens array structure of the present invention.

Referring to FIG. 22, the multiple optical probe has the tenth microlens array structure of the present invention wherein a first unit 110 has the microlens array 110 corresponding to that in the first to ninth microlens array structures of the present invention and a second unit 120 is located in the longitudinal direction with respect to the first unit 110 in such a manner as to have the traversely relative positioning with respect to the first unit 110, the second unit 120 having a microlens array structure where the microlenses M are located traversely and longitudinally.

As shown in FIG. 22, the second unit 120 has the same microlens array as the first unit 110, and alternatively, it may have the microlens array different from the first unit 110.

So as to allow the second unit 120 to have the traversely relative positioning with respect to the first unit 110, the microlens MF2 located in the traverse direction at one end portion of the second unit 120 has the traversely relative positioning with respect to the microlens ML1 located in the traverse direction at the other end portion of the first unit 110.

Accordingly, one end portion or intermediate portion of the microlens MF2 in the traverse direction thereof is partially overlapped with the microlens ML1 on the longitudinally continuous line, and according to the tenth microlens array structure of the present invention, scanning for a large area can be achieved at the same time, not through the first column 111 and the second column 112 continuously located in the traverse direction over the large area, but through the first and second units 110 and 120.

Accordingly, the number of the first and second units 110 and 120 is increased or decreased in accordance with the scanning area (width) of the measuring object, thus avoiding the need for separately manufacturing the multiple optical probe having the corresponding size to the scanning area of the measuring object, so that the large area can be scanned at the same time in more easy and efficient manners.

The first unit 110 has a unit 110a and a unit 110b spaced apart from each other in the traverse direction thereof, and the second unit 120 is located between the units 110a and 110b in such a manner as to have the traversely relative positioning with respect to the units 110a and 110b of the first unit 110.

The microlens MF2 located in the traverse direction at one end portion of the second unit 120 has the traversely relative positioning with respect to the microlens ML1 located in the traverse direction at the other end portion of the unit 110a of the first unit 110, and the microlens ML2 located in the traverse direction at the other end portion of the second unit 120 has the traversely relative positioning with respect to the microlens MF1 located in the traverse direction at one end portion of the unit 110b of the first unit 110, so that scanning can be carried out over the traverse width of the microlenses M constituting the plurality of first units 110 and the plurality of second units 120.

According to the first to tenth microlens array structures of the present invention, while the multiple optical probe or the measuring object is being moved in the longitudinal direction thereof, the measuring object can be continuously scanned over the rectangular area or linear area thereof corresponding to the traverse width of the microlenses M constituting the first column 111 and the second column 112 or the first unit 110 and the second unit 120.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A multiple parallel confocal system comprising:
a light source for irradiating light;
a relay lens unit through which the light traveling toward a measuring object or the light reflected from the measuring object is passed, the relay lens unit having one or more lens for focusing the light irradiated from the light source;
a multiple optical probe having a microlens array on which a plurality of microlenses is arranged, the microlenses into which the focused light through the relay lens unit is incident; and
a photo detector for detecting the incident light reflected from the measuring object and passed through the microlenses and the relay lens unit,
wherein a working distance between each microlens and the measuring object is increased, and a back focus determined by the focal distance of each microlens and the working distance between the microlens and the measuring object and a focus of the relay lens unit are located on the same plane, the back focus being calculated by the following expression:

$$BFL = f(f+x)/x$$

wherein f denotes the focal distance of each microlens and f+x denotes the distance between each microlens and the measuring object, and
wherein an aperture is disposed on a focal plane where the focuses of the relay lens unit and the back focuses of the microlenses meet, the aperture having pinholes formed thereon.

2. The multiple parallel confocal system according to claim 1, wherein the relay lens unit comprises an aperture.

3. The multiple parallel confocal system according to claim 1, wherein the relay lens unit comprises a telecentric lens.

4. The multiple parallel confocal system according to claim 3, wherein the light source is disposed above the optical axis of the telecentric lens.

5. The multiple parallel confocal system according to claim 3, wherein the light source is disposed under the optical axis of the telecentric lens.

6. The multiple parallel confocal system according to claim 4, further comprising a beam splitter adapted to convert the advancing paths of the light irradiated from the light source.

7. The multiple parallel confocal system according to claim 5, further comprising a beam splitter adapted to convert the advancing paths of the light irradiated from the light source.

8. The multiple parallel confocal system according to claim 1, wherein the multiple optical probe having the microlens array comprises: a first column along which the microlenses are arranged in the traverse direction thereof; and a second column along which the microlenses are arranged in the longitudinal direction with respect to the first column in such a manner as to allow a portion of each microlens to be located between the neighboring microlenses of the first column.

9. The multiple parallel confocal system according to claim 8, wherein the distance between the neighboring microlenses of the second column is the same as that of the first column in such a manner as to be located traversely with respect to the first column.

10. The multiple parallel confocal system according to claim 8, wherein the distance between the neighboring microlenses of the second column is different from that of the first column.

11. The multiple parallel confocal system according to claim 8, wherein the first column has a given distance shorter than the distance between the neighboring microlenses thereof, and the microlenses of the second column are partially protruded toward the distance between the neighboring microlenses of the first column or completely traverse the distance between the neighboring microlenses of the first column.

12. The multiple parallel confocal system according to claim 8, wherein the multiple optical probe having the microlens array further comprises a third column along which the microlenses are arranged in the longitudinal direction with respect to the first and second columns in such a manner as to be partially located between the microlenses of the first and second columns.

* * * * *